United States Patent [19]
Palmer

[11] Patent Number: 5,988,479
[45] Date of Patent: Nov. 23, 1999

[54] APPARATUS FOR APPLYING SURGICAL FASTENERS

[75] Inventor: Mitchell J. Palmer, New Milford, Conn.

[73] Assignee: United States Surgical Corporation, Norwalk, Conn.

[21] Appl. No.: 08/659,095

[22] Filed: Jun. 4, 1996

Related U.S. Application Data

[63] Continuation of application No. 08/354,996, Dec. 13, 1994, abandoned.

[51] Int. Cl.⁶ .................................................. A61B 17/068
[52] U.S. Cl. ..................... 227/175.4; 227/19; 227/176.1; 227/180.1; 227/182.1
[58] Field of Search .............................. 227/175.1, 176.1, 227/175.2, 175.3, 175.4, 180.1, 182.1, 8, 19

[56] References Cited

U.S. PATENT DOCUMENTS

| | | |
|---|---|---|
| D. 283,733 | 5/1986 | Rawson et al. . |
| D. 322,143 | 12/1991 | Spreckelmeier . |
| 2,174,219 | 9/1939 | Balma . |
| 2,246,647 | 6/1941 | Vancura . |
| 3,079,606 | 3/1963 | Bobrov et al. . |
| 3,490,675 | 1/1970 | Green et al. . |
| 3,494,533 | 2/1970 | Green et al. . |
| 3,499,591 | 3/1970 | Green . |
| 3,675,688 | 7/1972 | Bryan et al. . |
| 3,692,224 | 9/1972 | Astafiev et al. . |
| 3,735,762 | 5/1973 | Bryan et al. . |
| 3,795,034 | 3/1974 | Strekopytov et al. . |
| 3,844,289 | 10/1974 | Noiles . |
| 3,873,016 | 3/1975 | Fishbein . |
| 4,006,786 | 2/1977 | Speicher . |
| 4,086,926 | 5/1978 | Green et al. . |
| 4,108,306 | 8/1978 | Samuels et al. . |
| 4,202,479 | 5/1980 | Razgulov et al. . |

(List continued on next page.)

FOREIGN PATENT DOCUMENTS

| | | |
|---|---|---|
| 5476486 | 9/1986 | Australia . |
| 5476586 | 9/1986 | Australia . |
| 0324638 | 7/1989 | European Pat. Off. . |
| 0373762 | 6/1990 | European Pat. Off. . |
| 0380025 | 8/1990 | European Pat. Off. . |
| 0489436 | 6/1992 | European Pat. Off. . |
| 0596543 | 5/1994 | European Pat. Off. . |
| 2070499 | 9/1981 | United Kingdom . |
| 8302247 | 7/1983 | WIPO . |
| WO9523557 | 9/1995 | WIPO . |

OTHER PUBLICATIONS

Flickinger et al. Surgical Stapling Gastric and Small Bowel Procedures pp. 1–145, 1988.

Anderson et al. Surgical Stapling Thoraci, Vascular and Esophageal Procedures pp. 1–101, 1988.

Brolin et al. Surgical Stapling Bariatric Procedures for Morbid Obesity pp. 1–115, 1989.

"Auto Suture® Premium Poly CS™–57 Disposable Surgical Stapler," printed 1986, reprinted 1990.

"Auto Suture® Poly CS™–57 Disposable Surgical Stapler", printed Jul. 1988.

"Auto Suture® Poly CS™–57 Disposable Loading Units with Lactomer Absorbable Copolymer Staples", printed Jul. 1988.

U.S. application No. Re. 90/002,229, Fox et al., filed Nov. 27, 1990, issued Aug. 1991.

*Primary Examiner*—Scott A. Smith

[57] ABSTRACT

A surgical fastener applying apparatus having elongated cartridge and anvil half sections which are relatively movable from an unclamped to a clamped position. A safety member is supported in the cartridge section and movable between a non-blocking position and a blocking position to prevent relative movement of the cartridge and anvil support member to the clamped position after the fasteners have been fired. The safety member is biased inwardly by a tab retainer. Distal movement of the cam bars causes the tab retainer to be moved to a release position to allow movement of the safety tab to the blocking position.

27 Claims, 11 Drawing Sheets

U.S. PATENT DOCUMENTS

| | | |
|---|---|---|
| 4,202,480 | 5/1980 | Annett . |
| 4,256,251 | 3/1981 | Moshofsky . |
| 4,296,881 | 10/1981 | Lee . |
| 4,304,236 | 12/1981 | Conta et al. . |
| 4,305,539 | 12/1981 | Korolkov et al. . |
| 4,319,576 | 3/1982 | Rothfuss . |
| 4,331,276 | 5/1982 | Bourque . |
| 4,349,028 | 9/1982 | Green . |
| 4,354,628 | 10/1982 | Green . |
| 4,383,634 | 5/1983 | Green . |
| 4,391,401 | 7/1983 | Moshofsky . |
| 4,415,112 | 11/1983 | Green . |
| 4,429,695 | 2/1984 | Green . |
| 4,442,964 | 4/1984 | Becht . |
| 4,473,077 | 9/1984 | Noiles et al. . |
| 4,480,640 | 11/1984 | Becht . |
| 4,500,025 | 2/1985 | Skwor . |
| 4,506,670 | 3/1985 | Crossley . |
| 4,508,253 | 4/1985 | Green . |
| 4,519,532 | 5/1985 | Foslien . |
| 4,520,817 | 6/1985 | Green . |
| 4,523,695 | 6/1985 | Braun et al. . |
| 4,527,724 | 7/1985 | Chow et al. . |
| 4,530,453 | 7/1985 | Green . |
| 4,540,110 | 9/1985 | Bent et al. . |
| 4,556,058 | 12/1985 | Green . |
| 4,568,009 | 2/1986 | Green . |
| 4,569,346 | 2/1986 | Poirier . |
| 4,576,165 | 3/1986 | Green et al. . |
| 4,576,167 | 3/1986 | Noiles . |
| 4,589,582 | 5/1986 | Bilotti . |
| 4,591,085 | 5/1986 | Di Giovanni . |
| 4,592,498 | 6/1986 | Braun et al. . |
| 4,597,517 | 7/1986 | Wagdy . |
| 4,605,004 | 8/1986 | Di Giovanni et al. . |
| 4,606,344 | 8/1986 | Di Giovanni . |
| 4,606,345 | 8/1986 | Dorband et al. . |
| 4,607,636 | 8/1986 | Kula et al. . |
| 4,608,981 | 9/1986 | Rothfuss et al. . |
| 4,612,933 | 9/1986 | Brinkerhoff et al. . |
| 4,617,928 | 10/1986 | Alfranca . |
| 4,633,861 | 1/1987 | Chow et al. . |
| 4,633,874 | 1/1987 | Chow et al. . |
| 4,646,745 | 3/1987 | Noiles . |
| 4,664,305 | 5/1987 | Blake, III et al. . |
| 4,665,916 | 5/1987 | Green . |
| 4,684,051 | 8/1987 | Akopov et al. . |
| 4,714,187 | 12/1987 | Green . |
| 4,715,520 | 12/1987 | Roehr, Jr. et al. . |
| 4,728,020 | 3/1988 | Green et al. . |
| 4,741,336 | 5/1988 | Failla et al. . |
| 4,807,628 | 2/1989 | Peters et al. . |
| 4,809,898 | 3/1989 | Gassner et al. . |
| 4,850,355 | 7/1989 | Brooks et al. . |
| 4,863,088 | 9/1989 | Redmond et al. . |
| 4,869,415 | 9/1989 | Fox . |
| 4,881,544 | 11/1989 | Green . |
| 4,881,545 | 11/1989 | Isaacs et al. . |
| 4,892,244 | 1/1990 | Fox et al. . |
| 4,915,100 | 4/1990 | Green . |
| 4,938,408 | 7/1990 | Bedi et al. . |
| 4,941,623 | 7/1990 | Pruitt . |
| 4,955,959 | 9/1990 | Tompkins et al. . |
| 5,031,814 | 7/1991 | Tompkins et al. . |
| 5,040,715 | 8/1991 | Green et al. . |
| 5,065,929 | 11/1991 | Schulze et al. . |
| 5,071,052 | 12/1991 | Rodak et al. . |
| 5,074,454 | 12/1991 | Peters . |
| 5,083,695 | 1/1992 | Foslien et al. . |
| 5,100,042 | 3/1992 | Gravener et al. . |
| 5,106,008 | 4/1992 | Tompkins et al. . |
| 5,129,570 | 7/1992 | Schulze et al. . |
| 5,395,034 | 3/1995 | Allen et al. ............................... 227/19 |
| 5,413,267 | 5/1995 | Solyntjes et al. ..................... 227/175.4 |
| 5,447,265 | 9/1995 | Vidal et al. . |
| 5,462,215 | 10/1995 | Viola et al. ............................... 227/19 |
| 5,470,009 | 11/1995 | Rodak ...................................... 227/19 |

FIG_3A

APPARATUS FOR APPLYING SURGICAL FASTENERS

This is a continuation of application Ser. No. 08/354,996, filed on Dec. 13, 1994 now abandoned.

BACKGROUND

1. Technical Field

The apparatus relates to surgical fastener applying apparatus, and more particularly to fastener applying apparatus for sequentially firing fasteners having a safety member which prevents reclamping of the apparatus after the fasteners have been fired.

2. Background of Related Art

Surgical devices wherein tissue is first grasped or clamped between opposing jaw structure and then joined by surgical fasteners are well known in the art. In some instruments, a knife is provided to cut the tissue which has been joined by the fasteners. The fasteners are typically in the form of surgical staples, however, two-part polymeric fasteners are also utilized.

Such devices can comprise two elongated members which are used to capture or clamp tissue. Typically, one of the members carries a disposable cartridge which houses a plurality of staples arranged in at least two parallel rows while the other member comprises an anvil which defines a surface for forming the staple legs as the fasteners are driven from the cartridge. The two elongated members are clamped together to capture the tissue between the cartridge and staple forming surface of the anvil. After the two members are clamped, the stapling operation is effected by a pusher which travels longitudinally through the cartridge carrying member, with the pusher acting upon the staples to sequentially eject them from the cartridge. A knife may travel with the pusher between the staple rows to longitudinally cut the stapled tissue between the rows of staples. Such instruments are disclosed in U.S. Pat. No. 3,079,606 and U.S. Pat. No. 3,490,675.

A later stapler disclosed in U.S. Pat. No. 3,499,591 applies a double row of staples on each side of the incision. This is accomplished by providing a cartridge assembly in which a cam member moves through an elongated guide path between two sets of staggered stapling carrying grooves. Staple drive members are located within the grooves and are positioned in such a manner so as to be contacted by the longitudinally moving cam to effect ejection of the staples. Other examples of such staplers are disclosed in U.S. Pat. No. 4,429,695.

U.S. Pat. No. 4,955,959 to Tomkins, et al discloses a surgical stapler for sequentially firing staples which has a locking mechanism engagable with the cam bar retainer to prevent subsequent movement of the cam bar retainer after the staples have been fired. Thus, the user is prevented from cutting tissue if the cartridge is devoid of staples. Mechanisms for preventing refiring of a spent cartridge are also disclosed in U.S. Pat. No. 4,892,244 to Fox, et al, U.S. Pat. Nos. 5,156,315 and 5,253,793 to Green, et al and U.S. Pat. No. 5,129,570 to Schulze, et al.

WO 92/10976 to Plyley, et al discloses a surgical stapler which has a safety mechanism which prevents the two elongated members, i.e., the anvil carrying section and cartridge carrying section, from being reclamped after the staples have been fired and the elongated members unclamped and separated. A safety member is positioned in the cartridge assembly and is released for movement to a blocking position upon advancement of the cam bars to fire the staples. When the elongated cartridge and anvil carrying sections are separated, the safety member moves to the blocking position to prevent reclamping of the sections. EPO application 545029 to Allen, et al discloses another type of mechanism for preventing reclamping of the cartridge and anvil sections after they are separated subsequent to the fasteners being fired. In Allen, et al, the knife bar contacts the safety member to move it into the blocking position.

The need exists for an improved safety mechanism which would prevent reclamping of the anvil and cartridge on body tissue after the staples have been fired. This would advantageously inform the user that a new cartridge needs to be reloaded in the apparatus. Furthermore, by preventing reclamping, the user would not actuate the firing knob to advance the knife to cut tissue in the absence of a loaded cartridge.

SUMMARY

A surgical fastener applying apparatus is provided comprising an elongated cartridge section and an elongated anvil section relatively moveable from an unclamped position to a clamped position to clamp tissue between the cartridge and anvil. The firing knob moves the pair of cam bars longitudinally to sequentially fire the fasteners from the cartridge in a direction transverse to the direction of movement of the cam bars. A safety member is supported in the cartridge section and is mounted for movement between an initial position to allow relative movement of the cartridge and anvil sections to the clamped position and a blocking position to prevent relative movement of the cartridge and anvil sections to the clamped position after the fasteners have been fired. The safety member moves toward the blocking position in a direction away from the longitudinal axis of the cartridge towards an outer surface of the cartridge section. The safety member may be movable from the first position to the blocking position in a direction substantially transverse to the direction of movement of the cam bars and substantially transverse to the direction of movement of the fasteners.

The safety member preferably includes a pivotable safety tab and a sliding tab retainer. Sliding movement of the tab retainer to a release position allows the safety tab to pivot to a blocking position to prevent reclamping of the cartridge and anvil sections. The safety tab is preferably biased to the blocking position. Preferably the tab retainer slides to the release position upon distal movement of the firing knob as it is engaged by one of the cam bars upon distal movement thereof. In the blocking position, the safety tab preferably contacts one of the fingers of the tissue stop mounted on the anvil channel member.

DETAILED DESCRIPTION OF THE DRAWINGS

Various embodiments are described herein with reference to the drawings wherein.

DETAILED DESCRIPTION OF PREFERRED EMBODIMENTS

Figure 1:
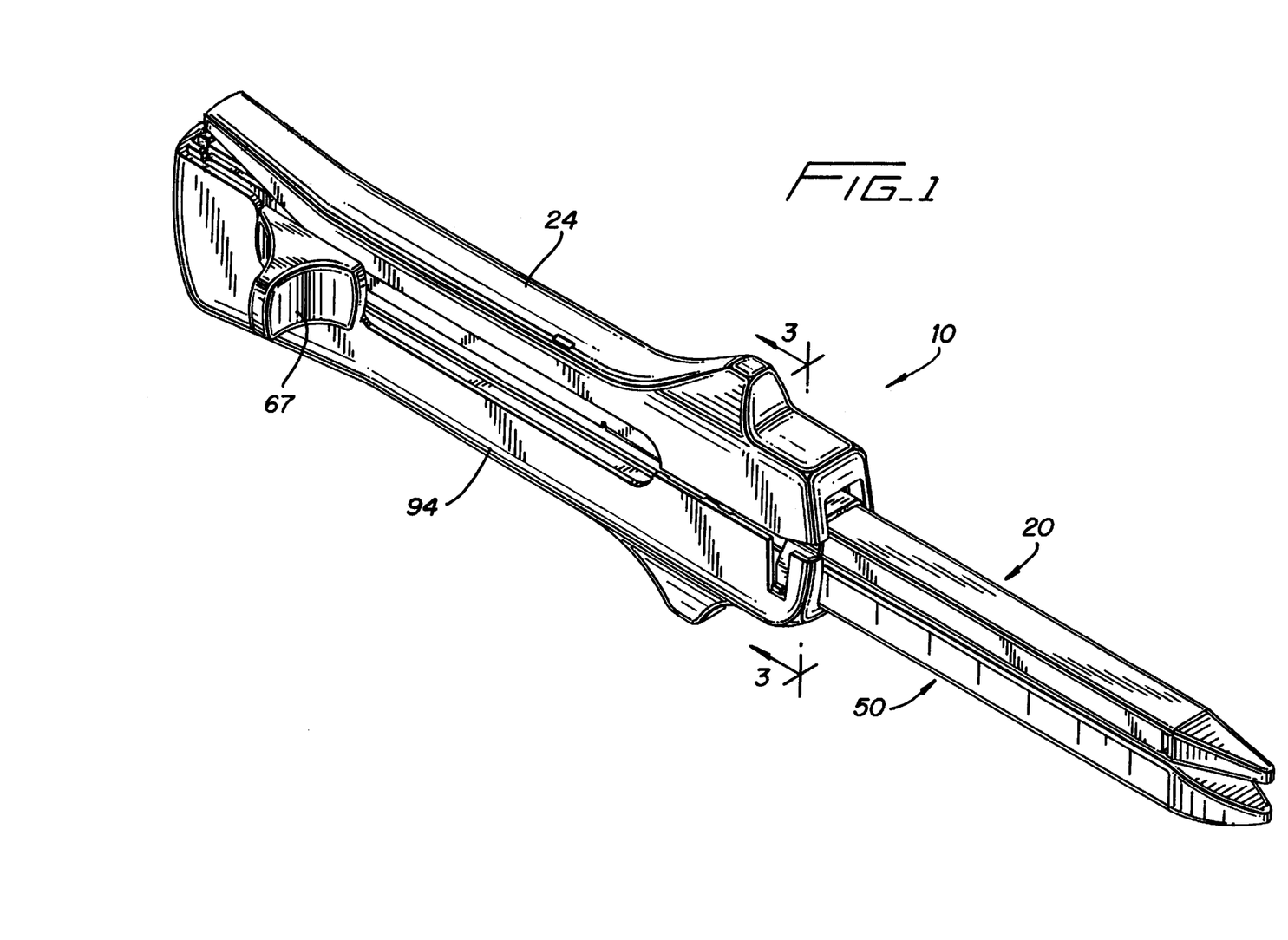
FIG. 1 is a perspective view illustrating the apparatus in the clamped and prefired position; 1
Figure 2:
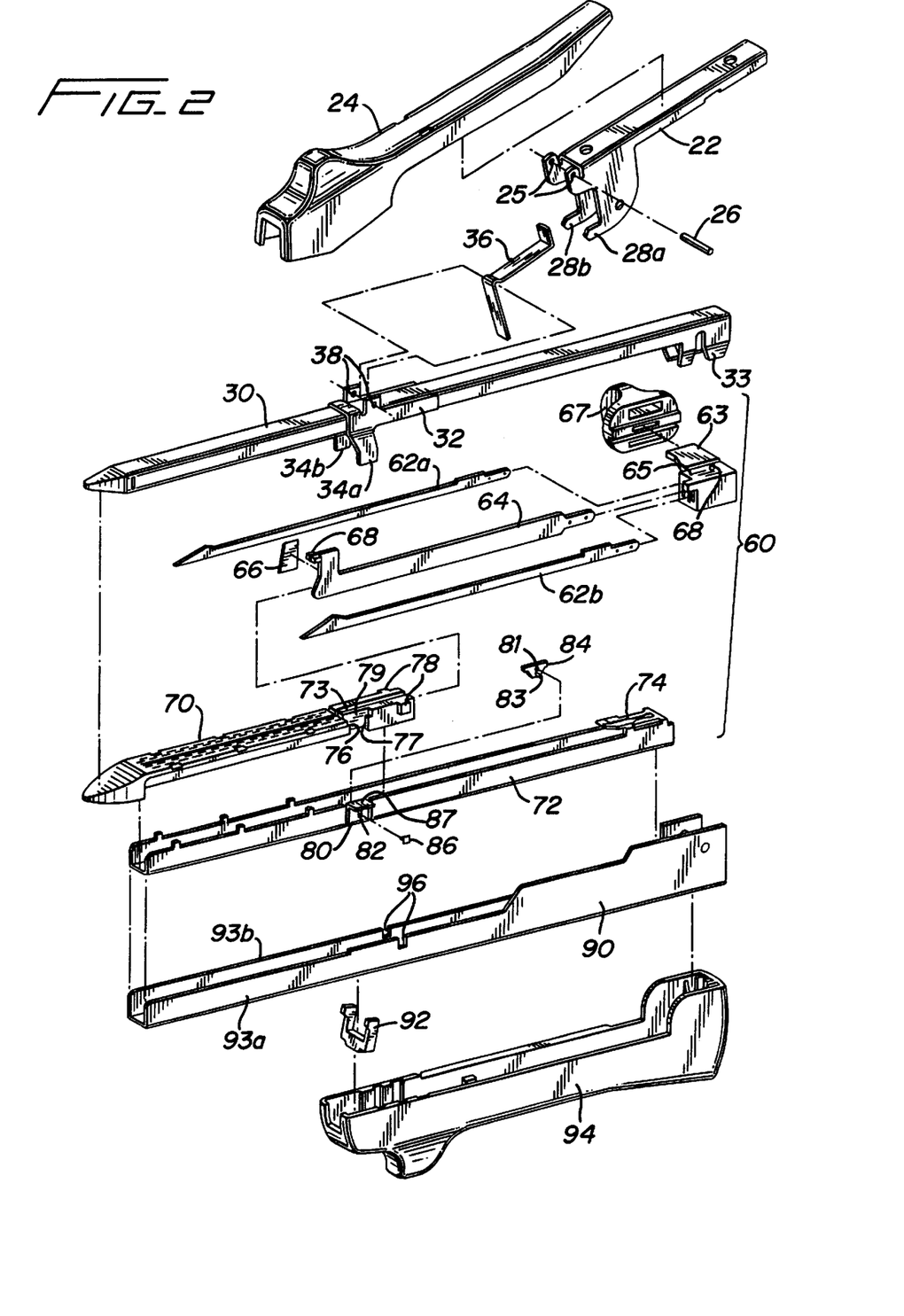
FIG. 2 is an exploded perspective view of the apparatus of FIG. 1.

Referring now to the drawings, and particularly to FIGS. 1 and 2, the apparatus 10 includes an anvil half section 20 and a cartridge half section 50. The anvil and cartridge half sections 20 and 50 are clamped together to bring cartridge 70 and the opposing anvil surface (not shown) of anvil channel 30 into close cooperative alignment to clamp body tissue therebetween. A firing knob 67 is slidable distally to sequentially fire a plurality of rows of fasteners, contained in cartridge 70, against the anvil surface. A safety tab is positioned in the cartridge half section 50 and is movable between a non-blocking position to allow the cartridge and anvil half sections 20, 50 to be clamped together and a blocking position to prevent clamping of the half sections after the fasteners have been fired and the half sections separated. The structure and function of the safety tab 80 is described in more detail below.

Turning first to the anvil half section (or anvil supporting section) 20, a clamping lever 22 is seated within clamping lever housing 24 and is pivotally mounted to anvil channel 30 via transverse mounting pin 26 extending through openings 25 of clamping lever 22 and openings 38 in tissue stop 32. Clamping lever 22 is biased away from anvil channel 30 to the unclamped position by lever spring 36, and has a pair of locking fingers 28a, 28b which slide underneath a channel clamp 92 in cartridge half section 50 described below. Anvil fork 33 of anvil channel 30 is configured to be mounted to a transverse pin (not shown) in the cartridge support member 90. Clamping fingers 34a, 34b of tissue stop 32 straddle the cartridge channel 90 to prevent lateral movement when the anvil and cartridge half sections 20, 50 are clamped together.

Cartridge half section (or cartridge supporting section) 50 includes a cartridge housing 94, a cartridge channel 90 snap fitted therein, and a disposable loading unit, designated generally by reference numeral 60, which is removably mounted in cartridge channel 90. U-shaped cartridge clamp 92 is mounted within housing 94 and cooperates with locking fingers 28a, 28b of clamping lever 22 (see FIG. 3A) such that pivotal movement of clamping lever 22 to the clamping position, i.e. towards the anvil channel 30, forces the cartridge channel 90 and anvil channel 30 towards each other bringing the anvil surface and cartridge into close cooperative alignment.

With continued reference to FIG. 2, the disposable loading unit 60 includes an elongated cartridge channel 72, cartridge 70, a pair of cam bars 62a, 62b, a knife bar 64 carrying a knife blade 66, a cam bar retainer 65 and a firing knob 67. Tabs 78 of cartridge 70 engage slots 96 formed in side walls 93 of cartridge channel 90 when the disposable loading unit 60 is mounted therein. The cam bars 62a, 62b and knife bar 64 are mounted at their proximal ends within respective slots in the cam bar retainer 65. Flange 63 of cam bar retainer 60 extends into a slot in the firing knob 67 such that movement of the firing knob slides the cam bar retainer 65 and mounted cam bars 62a, 62b, and knife bar 64 distally. The cartridge 70 preferably includes a plurality of metal staples arranged in four parallel rows, with each cam bar sequentially firing two rows of staples, and knife blade 66 which trails the cam bars cutting between the two pairs of staple rows. It should also be noted that as an alternative to metal staples, polymeric staples or two piece polymeric fasteners such as that disclosed in U.S. Pat. No. 5,253,793, can also be utilized, the contents of which is incorporated herein by reference.

Shoes 68, positioned on knife bar 64, slide within a slot within the anvil channel 30. The function of shoes 68 is described in U.S. Pat. No. 4,520,817, the contents of which are incorporated herein by reference.

Projection 69 of cam bar retainer 65 extends through shipping interlock 74 to prevent inadvertent movement of firing knob 67 during shipping or handling of the apparatus. When firing knob 67 is advanced to fire the staplers, projection 69 of cam bar retainer 65 travels into the widened slot portion of the shipping interlock 74.

Turning now to the safety mechanism of the apparatus, with continued reference to FIG. 2, the safety mechanism includes an L-shaped safety tab 80 which is formed out of the material in cartridge channel 72 and is spring biased outwardly away from the longitudinal axis of cartridge 70. A T-shaped tab retainer 84 is configured to retain safety tab 80 in a non-blocking position. Opening 81 receives a tab pin 86 which holds tab retainer 84 within slot 82 of the safety tab 80, and a guide pin 83 guides tab retainer 84 within the slot 82. Tab retainer 84 slides within a cartridge recess 76 in a direction substantially transverse to the longitudinal axis of the cartridge 70, i.e., substantially parallel to the direction of movement of the fasteners toward the anvil.

Cartridge recess 76 has a narrowed width portion 77 and a widened width portion 79 which will be discussed in more detail below. When tab retainer 84 is in its lowermost (initial) position as shown in FIGS. 3 and 3A–3C, the safety tab 80 is forced inwardly, i.e., away from wall 93a of cartridge channel 90. When tab retainer 84 is in the uppermost (release) position of cartridge recess 76, i.e., in the widened width portion 79, the safety tab 80 is allowed to return to its normal position such that upper surface 87 extends beyond the channel wall 93a. This uppermost position of tab retainer 84 is shown in FIGS. 4, 4A–4C, 5, and 5A. The movement of the tab retainer 84 from the initial retaining position to the upper release position occurs upon movement of the cam bar retainers in a manner discussed below.

Figure 3:
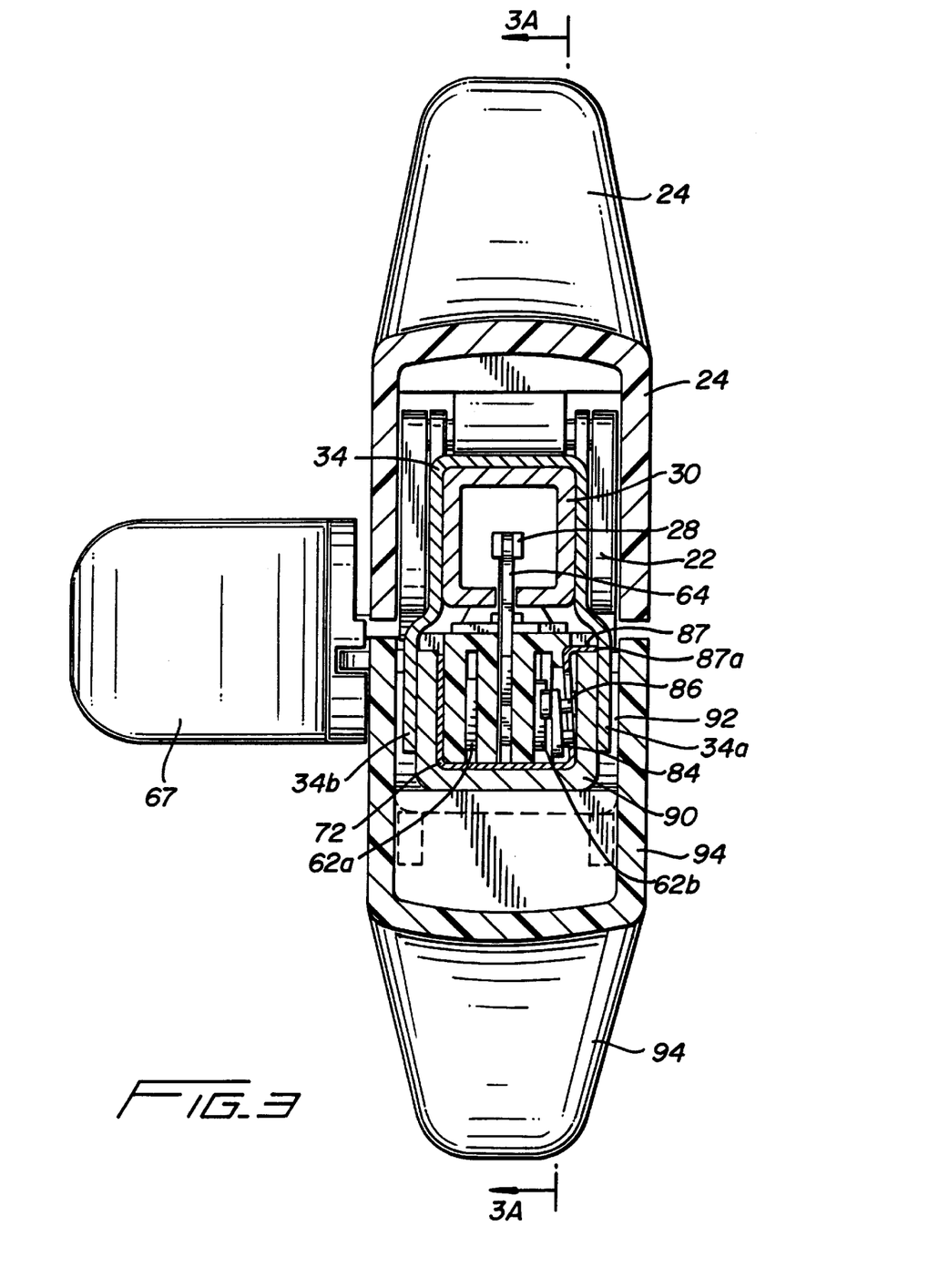
FIG. 3 is a cross-sectional view taken along lines 3—3 of FIG. 1 showing the safety tab in the initial (non-blocking) position.
Figure 3A:
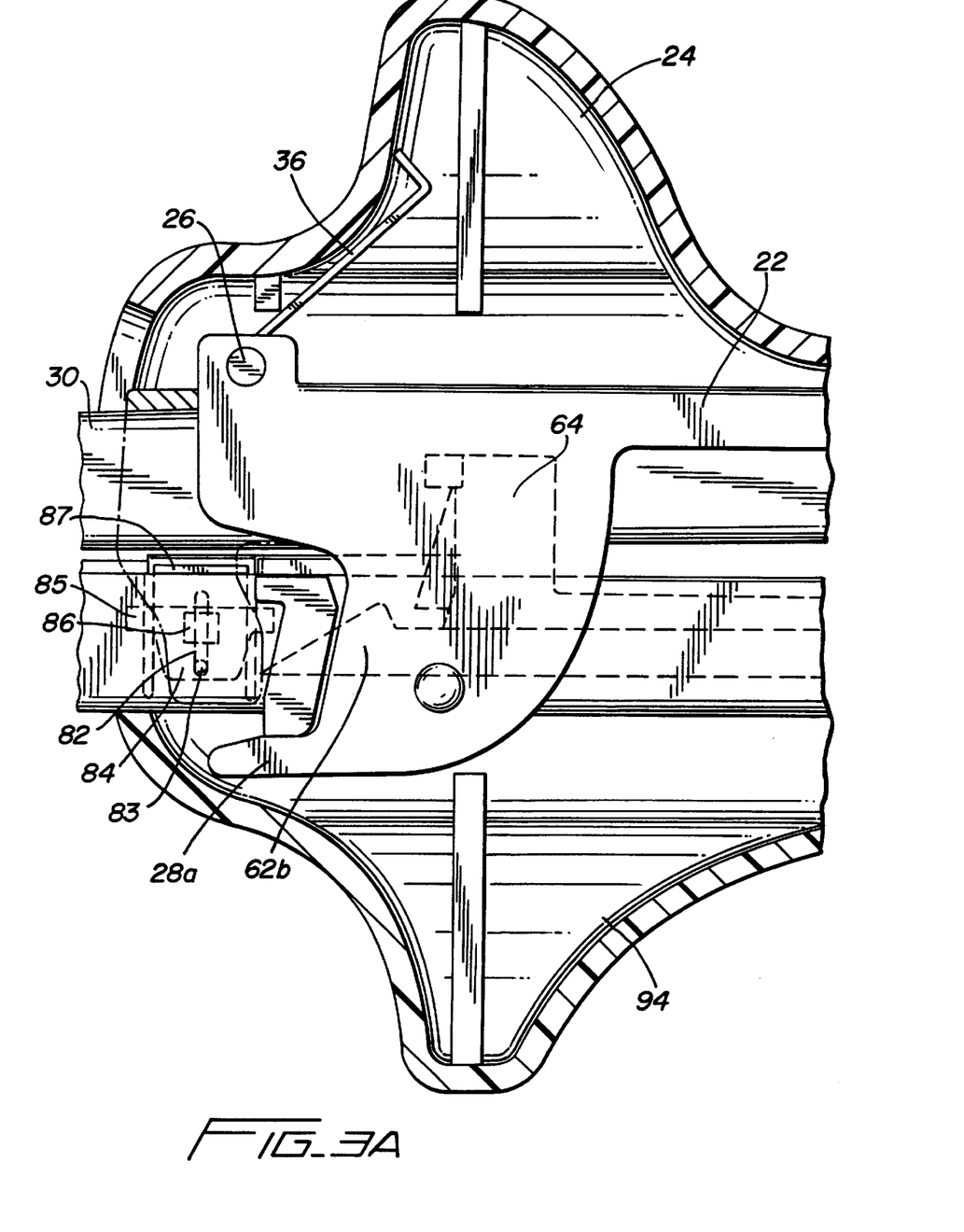
FIG. 3A is a cross-sectional view taken along lines 3A—3A of FIG. 3 showing the safety tab in the initial position.
Figure 3B:
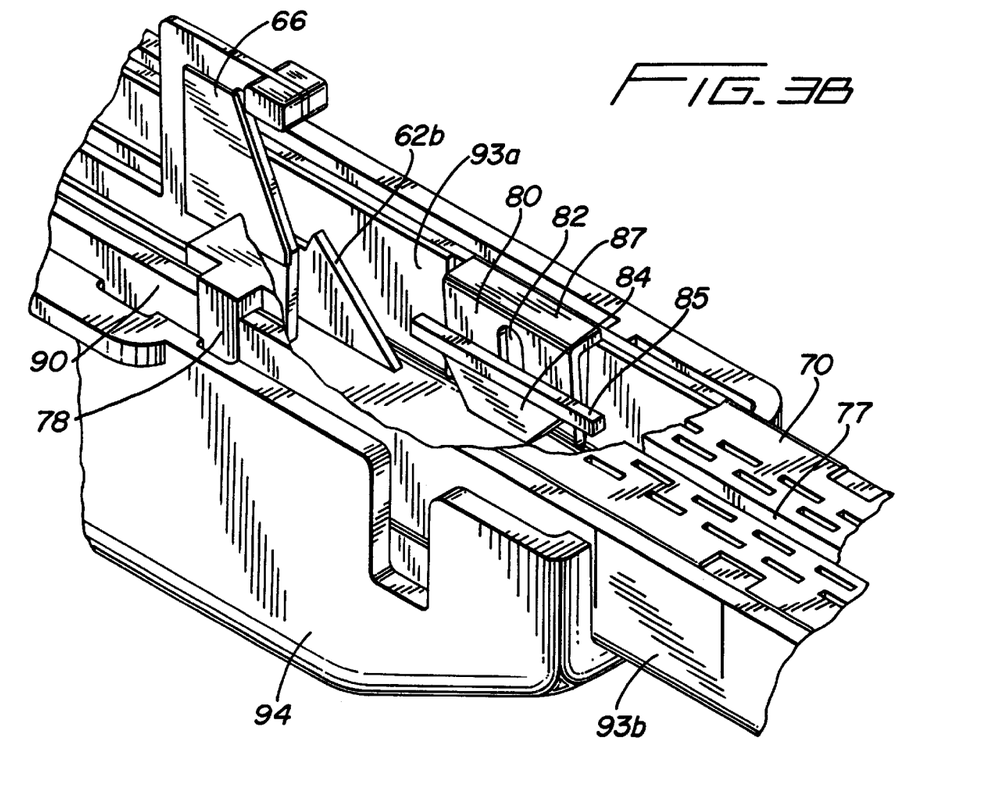
FIG. 3B is a perspective view with a portion of the cartridge cut away to illustrate the safety tab in the initial position.
Figure 3C:
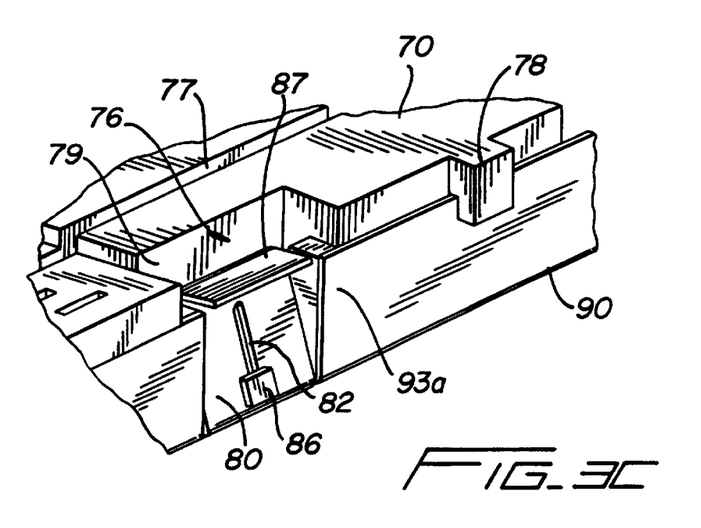
FIG. 3C is a perspective view illustrating the safety tab in the initial position of FIG. 3B.

In use, tissue is clamped between cartridge 70 and the anvil surface of anvil channel 30 as anvil fork 33 is mounted on the mounting pin of cartridge channel 90, clamping fingers 34 straddle cartridge channel 90, locking fingers 28a, 28b of clamping lever 22 are slid underneath cartridge clamp 92 and clamping lever 22 is pivoted towards anvil channel 30. Thus, the cartridge and anvil surface are placed in close cooperative alignment (see FIG. 1) and securely clamp tissue therebetween. Note that prior to firing the fasteners, (when firing knob 67 is in the proximalmost position of FIG. 1) tab retainer 84 is in the initial position biasing safety tab 80 inwardly so that upper surface 87 is out of contact with clamping fingers 34 (FIGS. 3, 3C). This allows the cartridge and anvil half sections to be clamped together. In this initial position of safety tab 80, shelf 85 of tab retainer 84 is retained in the narrowed width portion 77 of cartridge recess 76, thereby prohibiting pivotal movement of the tab retainer 84 (see FIGS. 3A, 3B).

Figure 4:
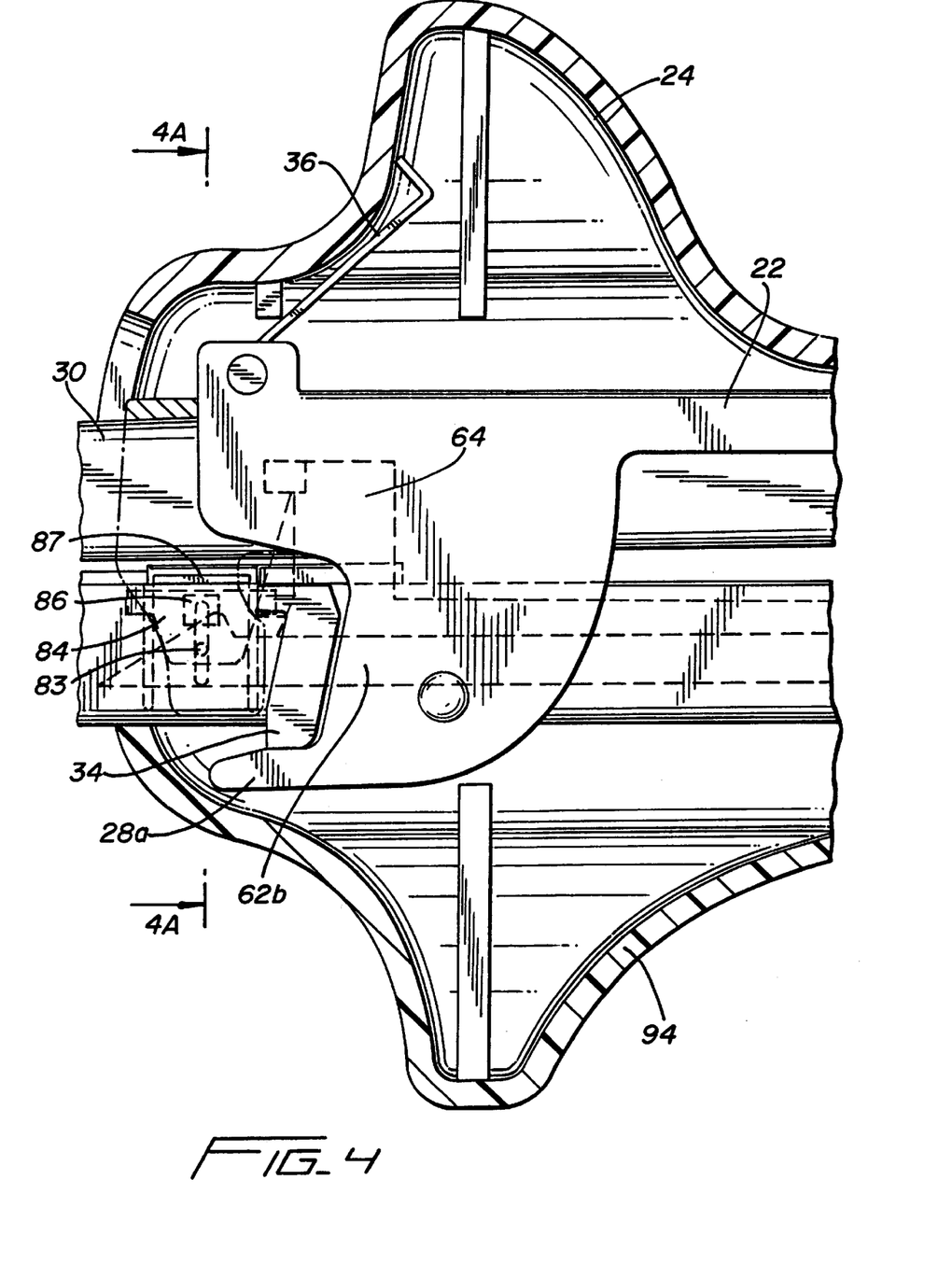
FIG. 4 is a cross-sectional view similar to the view of FIG. 3A except showing the tab retainer in the release position to allow movement of the safety tab to the blocking position.
Figure 4A:
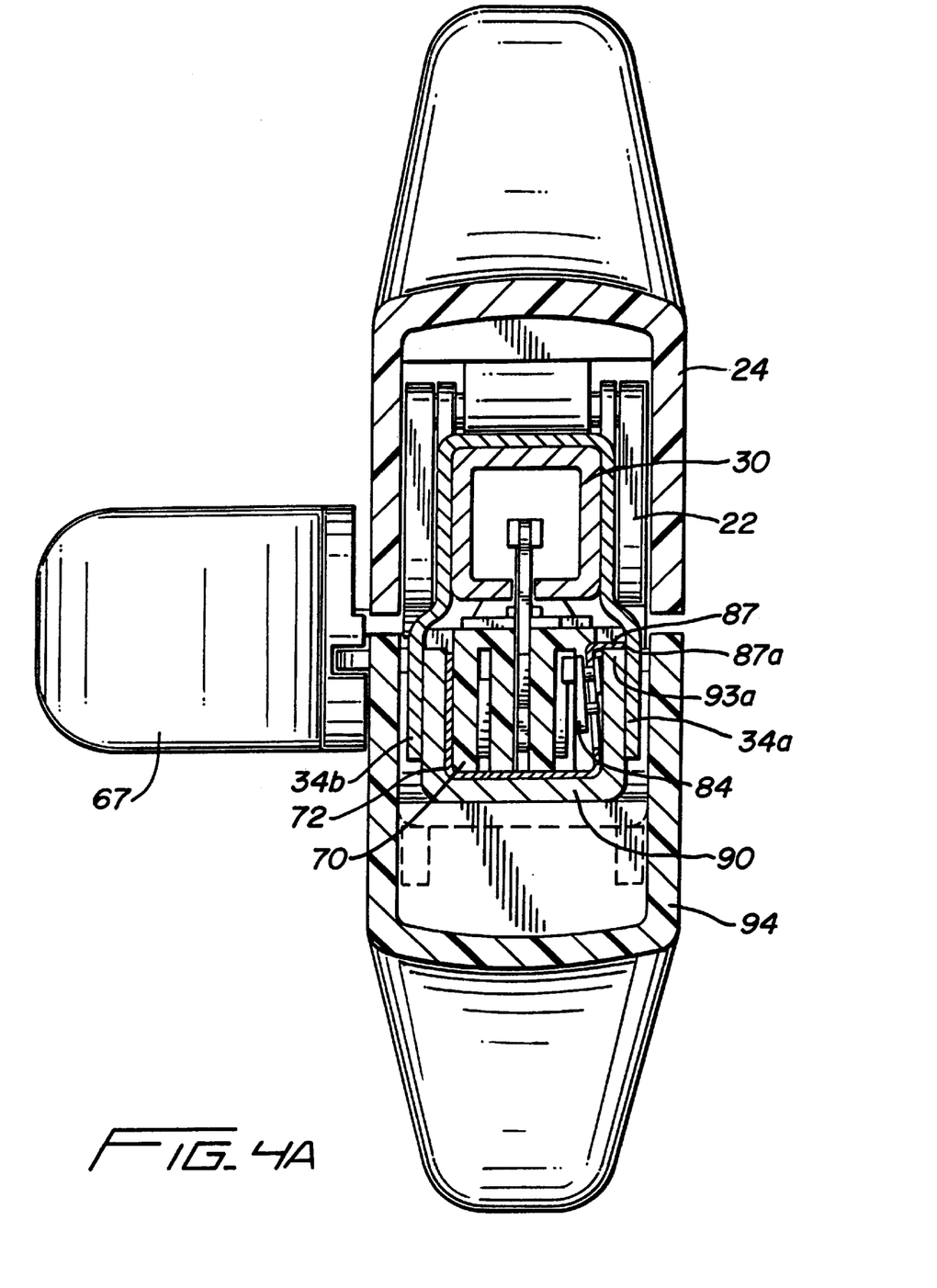
FIG. 4A is a cross-sectional view taken along lines 4A—4A of FIG. 4 showing the tab retainer in the release position.
Figure 4B:
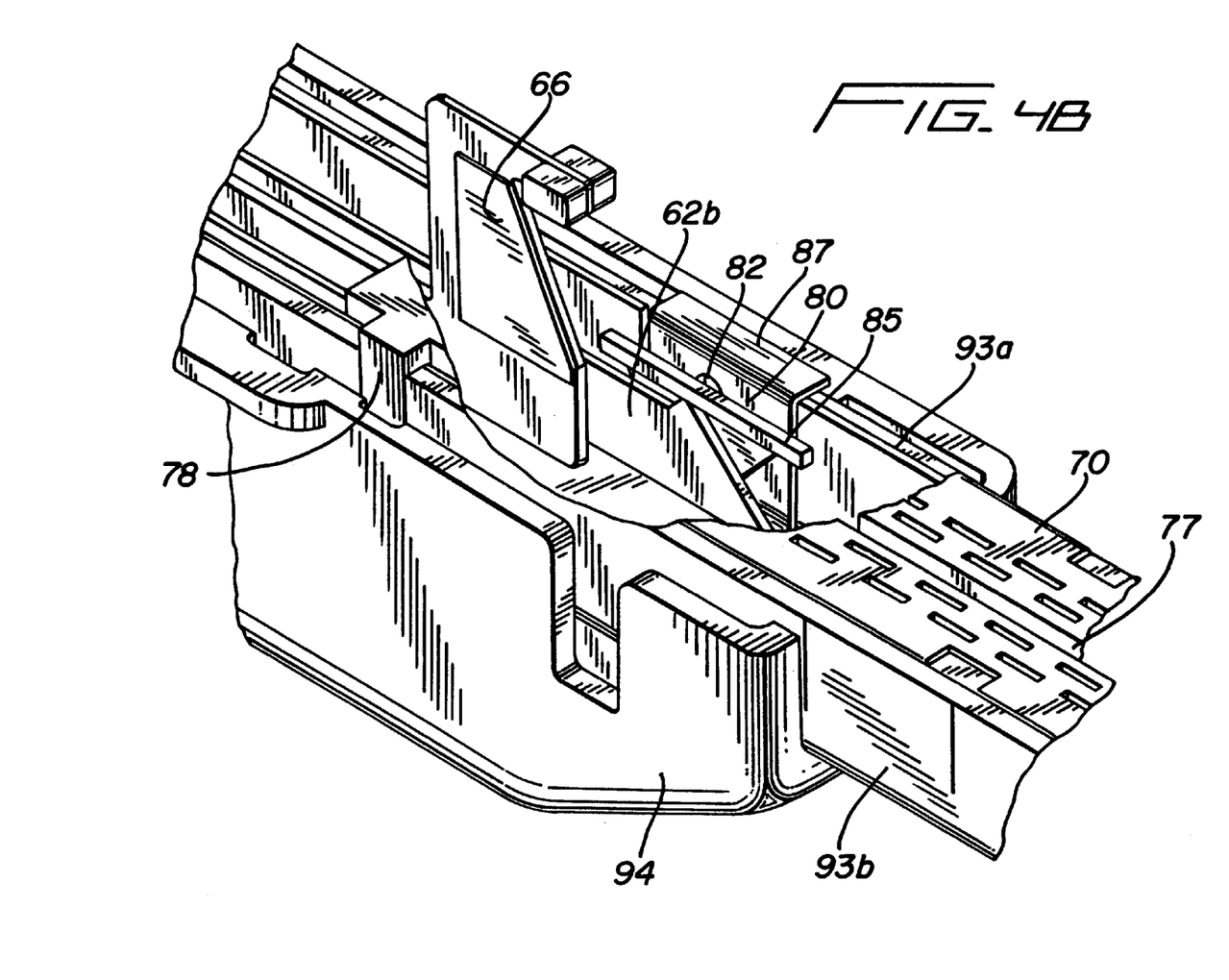
FIG. 4B is a perspective view with a portion of the cartridge cut away showing the tab retainer in the release position and the safety tab in the blocking position.
Figure 4C:
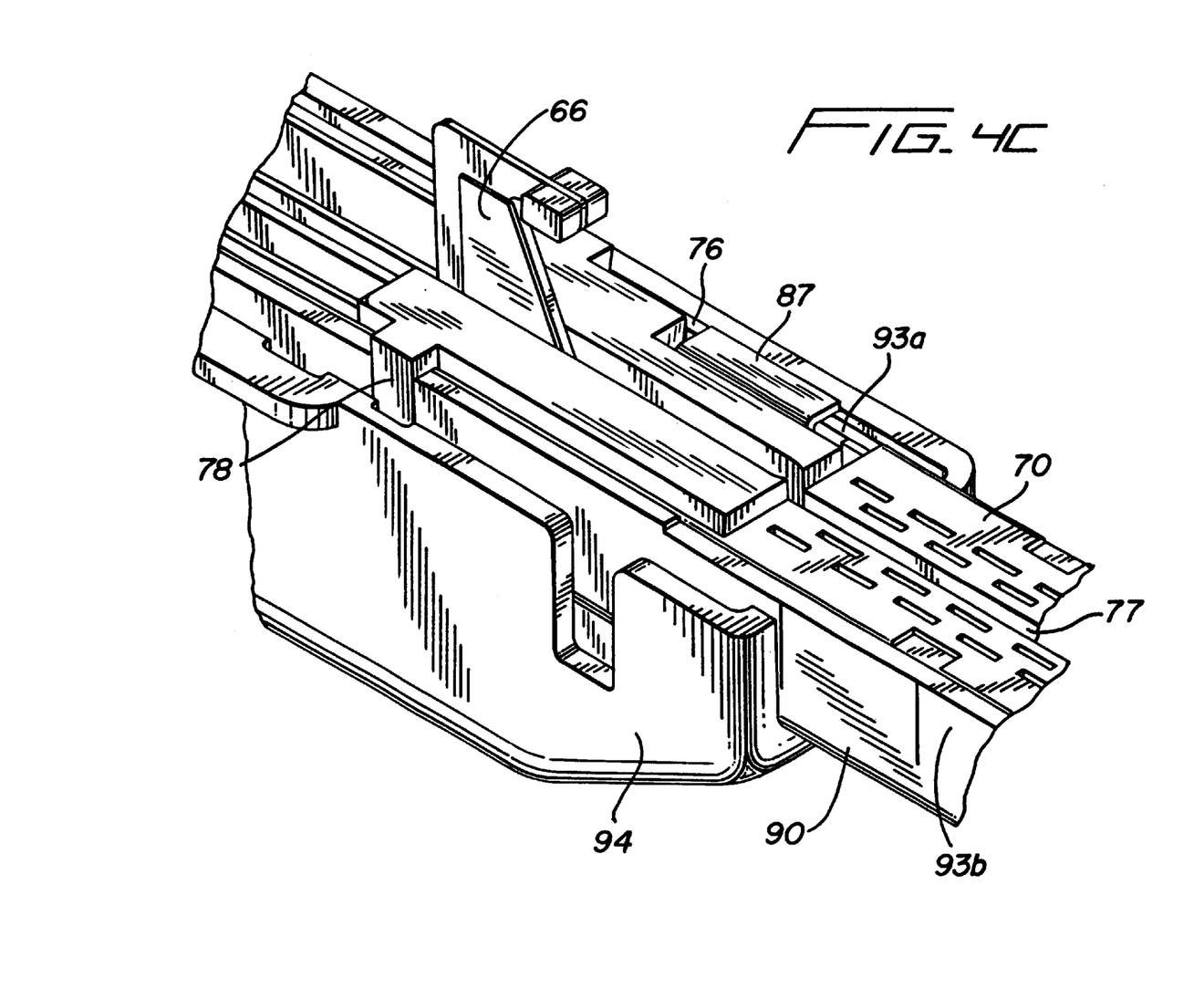
FIG. 4C is a perspective view of a portion of the cartridge half section showing the safety tab in the blocking position.

To fire the fasteners on the clamped tissue, firing knob 67 is slid longitudinally distally from its proximalmost position of FIG. 1, overcoming the aforementioned shipping interlock 74, and cam bars 62a, 62b, and knife bar 64 are moved distally. Prior to contacting the staple drivers positioned in cartridge 70, cam bar 62b contacts shelf 85 of tab retainer 84, as shown in FIG. 4B, and cams it upwardly within tab slot 82 to the release position. As shown, tab retainer 84 travels to its release position in a direction substantially transverse to the movement of the cam bar 62b, with guide pin 83 traveling in slot 82 (see FIGS. 4–4B). In this release position, shelf 85 is positioned in the widened width portion 79 of cartridge recess 76 and allows for release of the safety tab 80. However, as shown in FIG. 4A, the tip portion 87a of safety tab 80 contacts the inner surface of clamping finger 34a and is thus prevented from movement.

Figures 5, 5A:
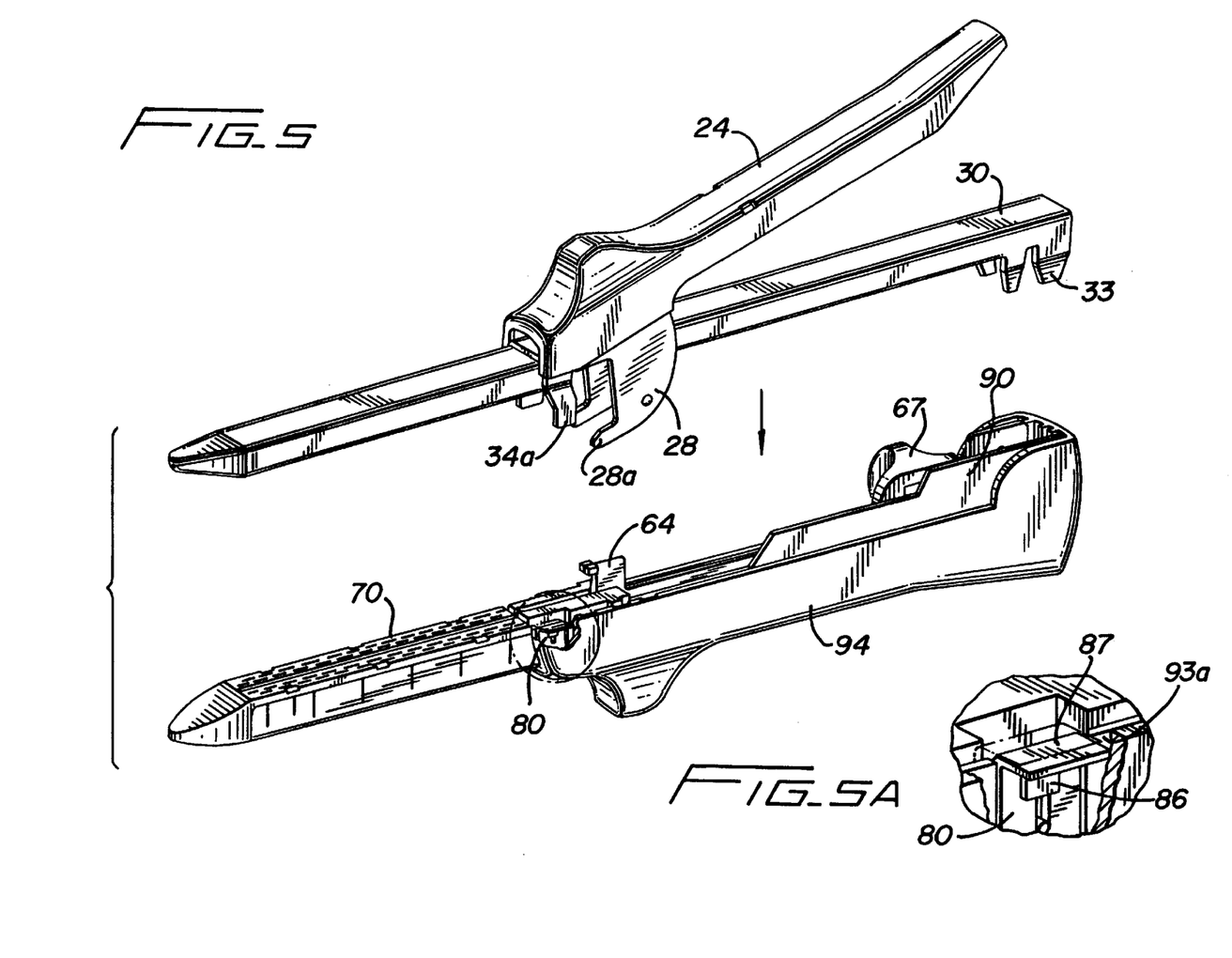
FIG. 5 is a perspective view illustrating the anvil and cartridge half sections separated and the safety tab in the blocking position.
FIG. 5A is an enlarged view of the safety tab in the blocking position.
Figures 6, 6A:
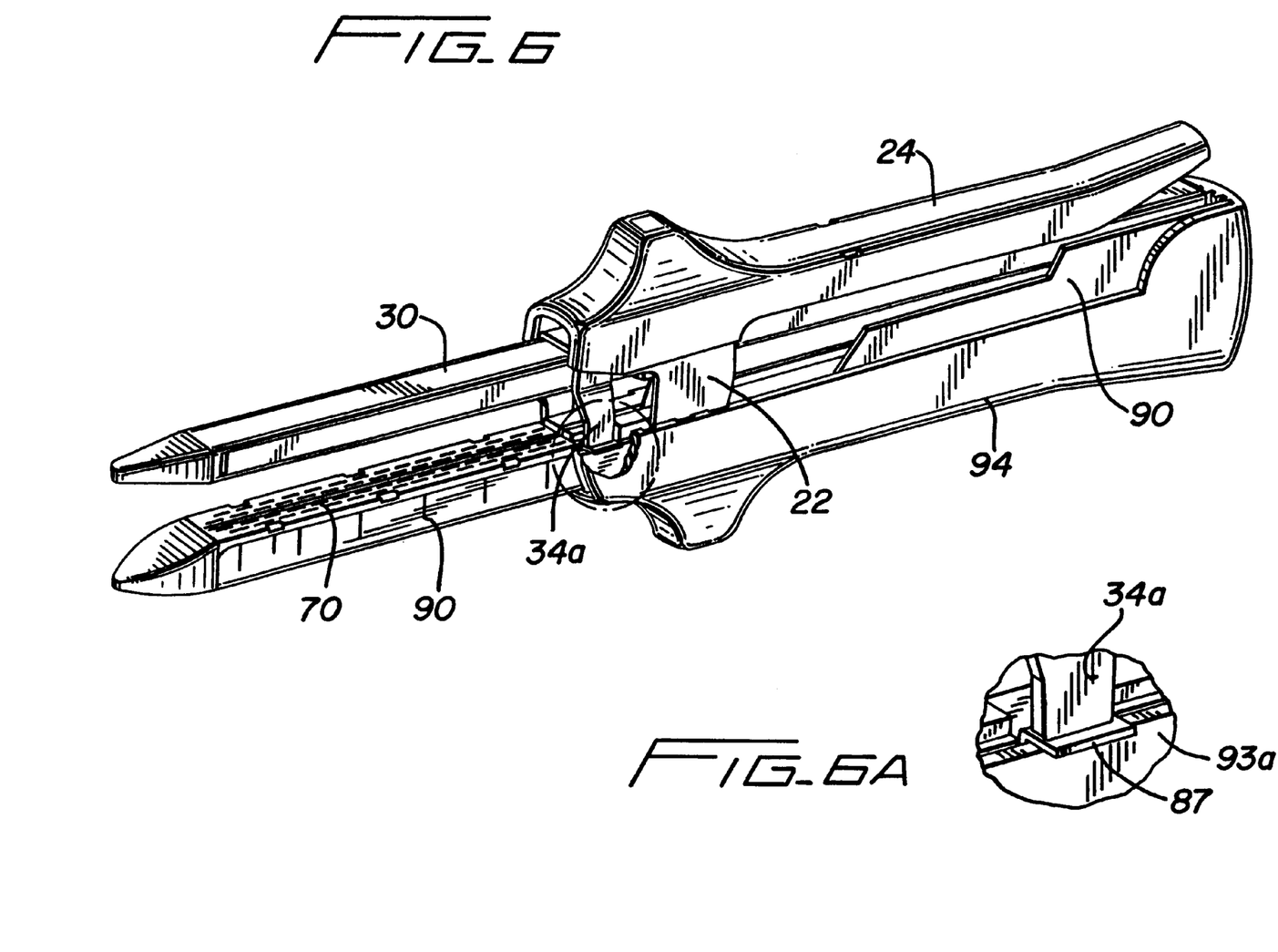
FIG. 6 is a perspective view illustrating the safety tab in the blocking position preventing reclamping of the anvil and cartridge half sections.
FIG. 6A is an enlarged view of the engagement of the safety tab and clamping fingers of the anvil half section to prevent reclamping of the apparatus.

When the anvil and cartridge half sections 20 and 50 are separated, and the clamping fingers 34a, 34b are removed from abutment with safety tab 80, safety tab 80 is allowed to pivot outwardly away from the longitudinal axis towards wall 93a of cartridge channel 90 to the blocking position shown in FIGS. 5 and 5A. In this blocking position, if the user attempts to reclamp the cartridge and anvil half sections 50, 20 as shown in FIGS. 6 and 6A, clamping finger 34a will abut the upper surface 87 of safety tab 80, thereby preventing the cartridge and anvil sections from being reassembled (reclamped). This will alert the user that the fasteners of the cartridge have been fired. The user can then remove the spent cartridge (with disposable loading unit 50) and replace it with a fresh disposable loading unit containing a loaded cartridge. The disposable loading unit with a loaded cartridge will have the safety tab 80 retained in the non-blocking position by the tab retainer and thereby allow reclamping of the cartridge and anvil half sections.

It is apparent that the safety mechanism prevents reclamping of the cartridge and anvil half sections if the cartridge is devoid of fasteners. Thus, if the half sections cannot be clamped, the user is alerted to the fact that a new disposable loading unit must be inserted. Also, unnecessary clamping on tissue is prevented.

It will be understood that various modifications may be made to the embodiments disclosed herein. Therefore, the above description should not be construed as limiting, but merely as exemplifications of preferred embodiments. Those skilled in the art will envision other modifications within the scope and spirit appended hereto.

What is claimed is:

1. A surgical fastener applying apparatus comprising:
   an elongated cartridge section having a longitudinal axis;
   an elongated anvil section, the cartridge and anvil sections being relatively movable from an unclamped position to a fully clamped position to clamp tissue therebetween;
   a plurality of cam bars positioned in the cartridge section;
   a cartridge containing a plurality of fasteners, the cartridge supported in the cartridge section and having a longitudinal axis;
   a firing knob operatively associated with the cam bars to move the cam bars longitudinally to sequentially fire the plurality of fasteners in a direction transverse to the direction of movement of the cam bars;
   a safety member supported in the cartridge section, the safety member mounted for movement between an initial position to allow relative movement of the cartridge and anvil sections to the clamped position and a blocking position to prevent relative movement of the cartridge and anvil sections to the clamped position after the fasteners have been fired, the safety member moving in a direction substantially transverse to the longitudinal axis of the cartridge and substantially transverse to the direction of movement of the fasteners.

2. A surgical fastener applying apparatus according to claim 1, further comprising a retainer tab slidably mounted to the safety member for movement from a retaining position to retain the safety member in a non-blocking position and a release position to allow movement of the safety member to the blocking position.

3. A surgical fastener applying apparatus according to claim 2, wherein the retainer tab includes a shelf, and one of the cam bars engages the shelf to slide the tab to the release position.

4. A surgical fastener applying apparatus according to claim 3, wherein the safety member includes an elongated slot to receive the retainer tab.

5. A surgical fastener applying apparatus according to claim 4, further comprising a pin securing the retainer tab within the elongated slot of the safety member.

6. A surgical fastener applying apparatus according to claim 5, wherein the retainer tab further comprises a guide pin slidably mounted within the slot.

7. A surgical fastener applying apparatus according to claim 3, further comprising a recessed portion in the cartridge to receive the tab retainer.

8. A surgical fastener applying apparatus according to claim 2, wherein the safety member is spring biased to the blocking position.

9. A surgical fastener applying apparatus according to claim 8, wherein the anvil section includes an anvil channel member and a tissue stop extending therefrom, the tissue stop contacting the safety member in the blocking position to prevent relative movement of the cartridge and anvil sections to the clamped position.

10. A surgical fastener applying apparatus according to claim 9, wherein the tissue stop includes first and second fingers, the first finger contacting the safety member in the blocking position to prevent relative movement of the cartridge and anvil sections to the clamped position.

11. A surgical fastener applying apparatus according to claim 2, wherein movement of the cartridge and anvil sections to the unclamped position after the fasteners have been fired allows movement of the safety member to the blocking position.

12. A surgical fastener applying apparatus according to claim 11, wherein the cartridge section includes an elongated cartridge support, a portion of the safety member extending laterally beyond an outer wall of the cartridge support in the blocking position.

13. A surgical fastener applying apparatus comprising:
- an elongated cartridge supporting member having a longitudinal axis and first and second substantially parallel outer walls;
- an elongated anvil supporting member, the cartridge and anvil supporting members being relatively movable from an unclamped position to a clamped position to clamp tissue therebetween;
- a tissue stop mounted to the anvil supporting member;
- a plurality of cam bars supported in the cartridge supporting member;
- a plurality of fasteners supported in the cartridge supporting member;
- a firing knob operatively associated with the cam bars to move the cam bars longitudinally to sequentially fire the plurality of fasteners in a direction transverse to the direction of movement of the cam bars; and
- a blocking member supported in the cartridge supporting member and mounted for movement between a non-blocking position to allow relative movement of the cartridge and anvil supporting members to the clamped position and a blocking position to prevent relative movement of the cartridge and anvil supporting members to the clamped position after the fasteners have been fired, the blocking member contacting the tissue stop in the blocking position.

14. A surgical fastener applying apparatus according to claim 13, wherein the blocking member pivots toward the blocking position in a direction away from the longitudinal axis of the cartridge support member and toward the first outer wall of the cartridge support member.

15. A surgical fastener applying apparatus according to claim 13, wherein the blocking member is biased toward the blocking position.

16. A surgical fastener applying apparatus according to claim 15, wherein movement of the cam bar distally releases the blocking member to allow movement towards the blocking position.

17. A surgical fastener applying apparatus according to claim 16, further comprising a retaining member for holding the blocking member in the non-blocking position, wherein movement of the cam bars distally causes one of the cam bars to engage and cam the retaining member to a release position to release the blocking member.

18. A surgical fastener applying apparatus according to claim 17, wherein the retaining member is cammed in a direction substantially parallel to the direction of movement of the fasteners.

19. A surgical fastener applying apparatus according to claim 18, wherein the retaning member includes a shelf which is engageable by one of the cam bars.

20. A surgical fastener applying apparatus according to claim 13, wherein the tissue stop includes first and second fingers, the first finger contacting the blocking member in the blocking position to prevent relative movement of the cartridge and anvil sections to the clamped position.

21. A surgical fastener applying apparatus according to claim 20, wherein in the non-blocking position, the first finger is in abutment with a first surface of the blocking member and in the blocking position the first finger is in contact with a second surface of the blocking member.

22. A surgical fastener applying apparatus comprising:
- an elongated cartridge section;
- an elongated anvil section, the cartridge and anvil sections being relatively movable from an unclamped position to a fully clamped position to clamp tissue therebetween;
- a plurality of cam bars supported in the cartridge section;
- a plurality of fasteners supported in the cartridge section;
- a firing knob operatively associated with the cam bars to move the cam bars longitudinally to sequentially fire the plurality of fasteners in a direction transverse to the direction of movement of the cam bars;
- a safety mechanism supported in the cartridge section, the safety mechanism including a pivotable safety tab and a sliding tab retainer, wherein sliding movement of the tab retainer to a release position allows the safety tab to pivot to a blocking position to prevent reclamping of the cartridge and anvil sections, the tab retainer sliding to the release position upon distal movement of the firing knob.

23. A surgical fastener applying apparatus according to claim 22, wherein the tab retainer is engagable by one of the cam bars upon distal movement of the firing knob to move the tab retainer to the release position.

24. A surgical fastener applying apparatus according to claim 23, wherein the safety tab is substantially L-shaped in configuration and is biased to a blocking position.

25. A surgical fastener applying apparatus according to claim 24, wherein the safety tab is movable to the blocking position in a direction substantially transverse to the direction of movement of the fasteners.

26. A surgical fastener applying apparatus according to claim 24, further comprising a pin securing the tab retainer to the safety tab.

27. A surgical fastener applying apparatus according to claim 26, wherein the safety tab includes an elongated slot to receive a guide pin of the tab retainer.

* * * * *